US00PP37717P2

(12) United States Plant Patent
van der Meer

(10) Patent No.: US PP37,717 P2
(45) Date of Patent: Sep. 29, 2026

(54) ***ASTILBE* PLANT NAMED 'HVDM18P'**

(50) Latin Name: *Astilbe chinensis*
Varietal Denomination: HVDM18P

(71) Applicant: Hans van der Meer, Nieuwe Wetering (NL)

(72) Inventor: Hans van der Meer, Nieuwe Wetering (NL)

( * ) Notice: Subject to any disclaimer, the term of this patent is extended or adjusted under 35 U.S.C. 154(b) by 0 days.

(21) Appl. No.: 19/549,701

(22) Filed: Feb. 25, 2026

(51) Int. Cl.
*A01H 6/80* (2018.01)
*A01H 5/02* (2018.01)

(52) U.S. Cl.
USPC ..... Plt./407

(58) Field of Classification Search
USPC ..... Plt./407
CPC ..... A01H 6/80; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Astilbe* plant named 'HVDM18P', characterized by its broadly upright plant habit with upright inflorescences; vigorous growth habit; thick and strong stems; dark green-colored leaves; freely and uniformly flowering habit; long flowering period; tall and broad inflorescences; bright purple-colored flowers on strong peduncles; and good container and garden performance.

3 Drawing Sheets

Figure 1:
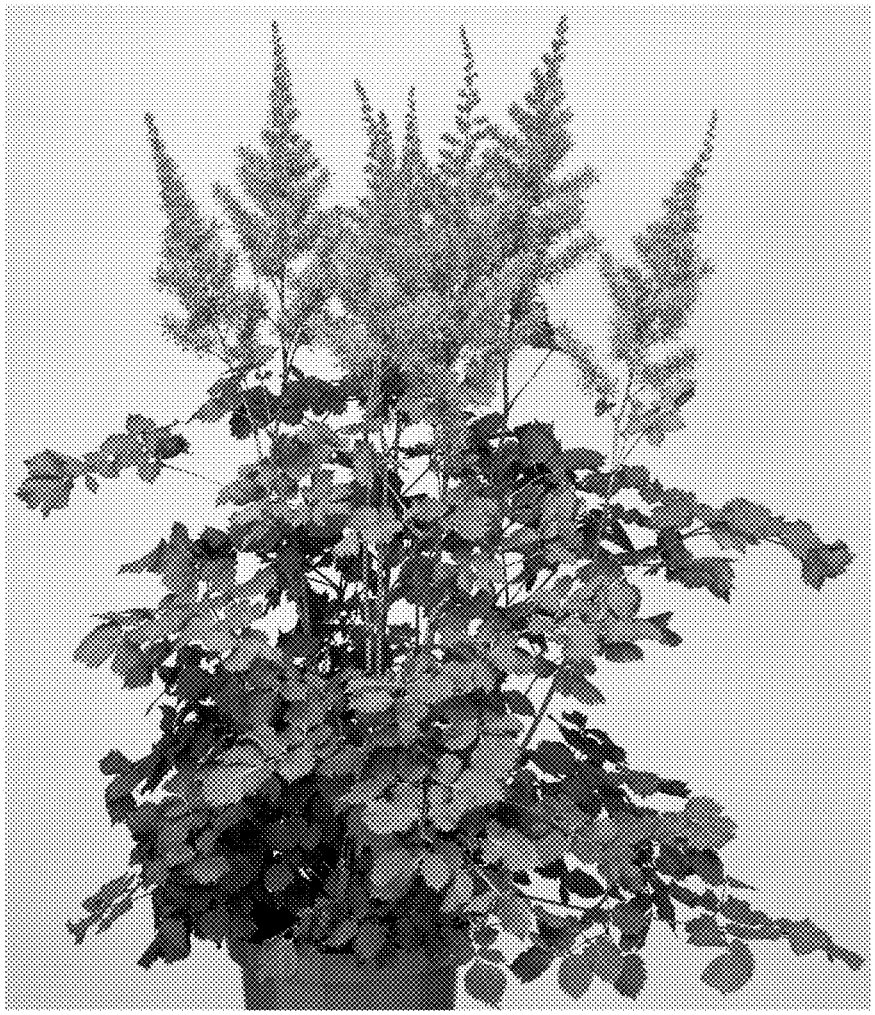

Botanical designation: *Astilbe chinensis.*
Cultivar denomination: 'HVDM18P'.

CROSS-REFERENCED TO CLOSELY-RELATED APPLICATION

A European Community Plant Breeder's Rights application for the instant plant was filed by the Inventor's company, Maatschap Dhr. J.W.M. van der Meer en Mw. E.H. van der Meer-Godijn of Nieuwe Wetering, The Netherlands on Feb. 10, 2026, application number 2437541, and to date, not published. Foreign priority is not claimed to this European Community Plant Breeder's Rights application.

BACKGROUND OF THE INVENTION

The present invention relates to a new and distinct cultivar of *Astilbe*, botanically known as *Astilbe chinensis* and hereinafter referred to by the name 'HVDM18P'.

The new *Astilbe* plant is a product of a planned breeding program conducted by the Inventor in Nieuwe Wetering, The Netherlands. The objective of the breeding program was to create new compact, uniform and freely flowering *Astilbe* plants with attractive leaf and flower coloration.

The new *Astilbe* plant originated from a cross-pollination in 2018 in Nieuwe Wetering, The Netherlands, of two unidentified seedling selections of *Astilbe chinensis*, not patented. The new *Astilbe* plant was discovered and selected by the Inventor as a single flowering plant from within the progeny of the stated cross-pollination in a controlled greenhouse environment in Nieuwe Wetering, The Netherlands in June, 2020.

Asexual reproduction of the new *Astilbe* plant by vegetative divisions in a controlled nursery environment in Nieuwe Wetering, The Netherlands since February, 2021, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HVDM18P'. These characteristics in combination distinguish 'HVDM18P' as a new and distinct *Astilbe* plant:

1. Broadly upright plant habit with upright inflorescences.
2. Vigorous growth habit.
3. Thick and strong stems.
4. Dark green-colored leaves.
5. Freely and uniformly flowering habit.
6. Long flowering period.
7. Tall and broad inflorescences.
8. Bright purple-colored flowers on strong peduncles.
9. Good container and garden performance.

Plants of the new *Astilbe* differ primarily from plants of the female parent selection in the following characteristics:

1. Plants of the new *Astilbe* are taller than plants of the female parent selection.
2. Inflorescences of plants of the new *Astilbe* are taller and broader than inflorescences of plants of the female parent selection.
3. Flowers of plants of the new *Astilbe* are lighter purple in color than flowers of plants of the female parent selection.

Plants of the new *Astilbe* differ primarily from plants of the male parent selection in the following characteristics:

1. Plants of the new *Astilbe* are taller than plants of the male parent selection.
2. Inflorescences of plants of the new *Astilbe* are taller and broader than inflorescences of plants of the male parent selection.

Plants of the new *Astilbe* can be compared to plants of *Astilbe chinensis* 'Visions', not patented. In side-by-side comparisons, plants of the new *Astilbe* and 'Visions' differ primarily in the following characteristics:

1. Plants of the new *Astilbe* are taller than plants of 'Visions'.
2. Inflorescences of plants of the new *Astilbe* are broader than inflorescences of plants of 'Visions'.
3. Flowers of plants of the new *Astilbe* are lighter purple in color than flowers of plants of 'Visions'.

Plants of the new *Astilbe* can also be compared to plants of *Astilbe chinensis* 'Purpurkerze', not patented. In side-by-side comparisons, plants of the new *Astilbe* and 'Purpurkerze' differ primarily in the following characteristics:

1. Plants of the new *Astilbe* are taller than plants of 'Purpurkerze'.
2. Inflorescences of plants of the new *Astilbe* are broader than inflorescences of plants of 'Purpurkerze'.
3. Flowers of plants of the new *Astilbe* are bright purple in color whereas flowers of plants of 'Purpurkerze' are dark pink in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1) is a side perspective view of a typical flowering plant of 'HVDM18P' grown in a container.

Figure 2:
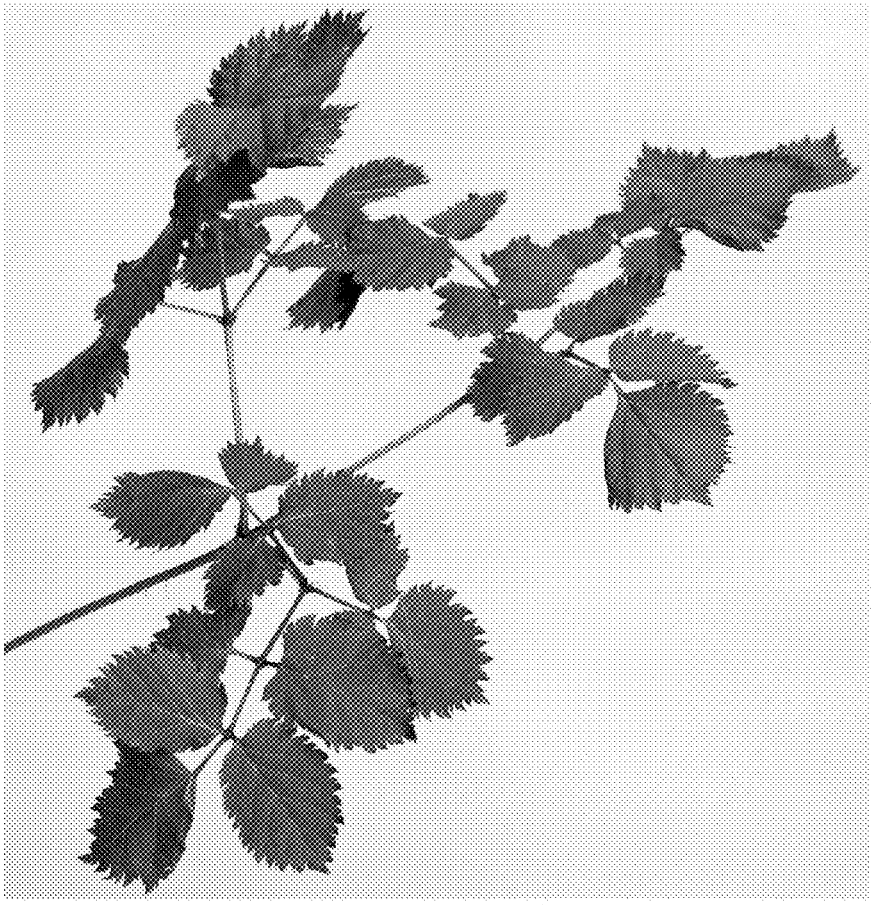

The photograph on the second sheet (FIG. 2) is a close-up view of typical leaves and leaflets of 'HVDM18P'.

Figure 3:
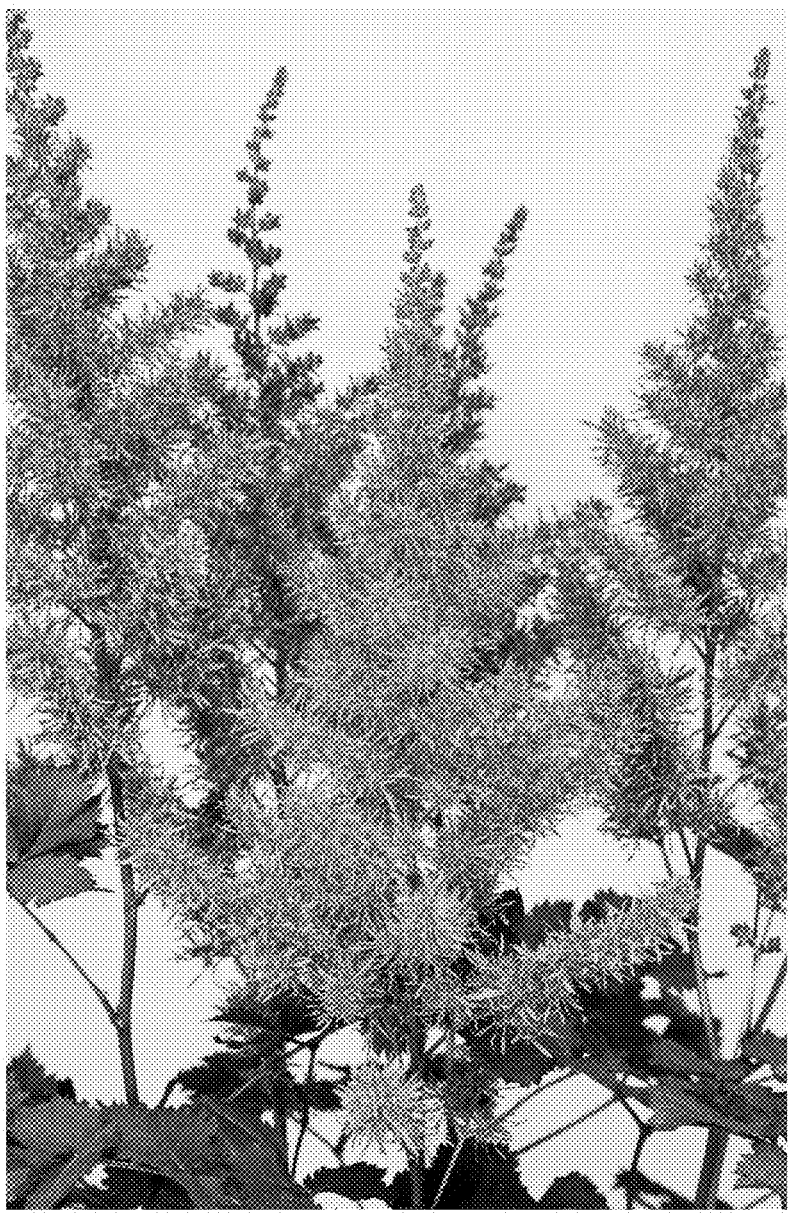

The photograph on the third sheet (FIG. 3) is a close-up view of typical inflorescences of 'HVDM18P'.

DETAILED BOTANICAL DESCRIPTION

The aforementioned photographs and following observations, measurements and values describe plants grown during the late summer and early autumn in 21-cm containers in an outdoor nursery in Nieuwe Wetering, The Netherlands and under cultural practices typical of commercial *Astilbe* production. During the production of the plants, day temperatures ranged from 18° C. to 32° C. and night temperatures ranged from 10° C. to 20° C. Plants were two years old when the photographs and description were taken. In the following description, color references are made to The Royal Horticultural Society Colour Chart, Sixth Edition, 2019 reprint, except where general terms of ordinary dictionary significance are used.

Botanical classification: *Astilbe chinensis* 'HVDM18P'.

Parentage:

*Female, or seed, parent*.—Unidentified seedling selection of *Astilbe chinensis*, not patented.

*Male, or pollen, parent*.—Unidentified seedling selection of *Astilbe chinensis*, not patented.

Propagation:

*Type*.—By vegetative divisions.

*Time to initiate roots*.—About three weeks at temperatures about 20° C.

*Root description*.—Thick, fleshy; typically brown in color, actual color of the roots is dependent on substrate composition, water quality, fertilizer type and formulation.

*Rooting habit*.—Freely branching; dense.

Plant description:

*Plant form and growth habit*.—Herbaceous perennial; broadly upright plant habit, overall plant shape, broadly oblong to broadly ovate, with inflorescences held above the foliar plane on upright and strong peduncles; flowering stems and leaves basal; freely flowering with numerous basal branches developing per plant, dense and bushy appearance; vigorous growth habit; and freely and uniformly flowering habit.

*Growth rate*.—Moderately rapid; from divisions, about three months are required to produce fully-grown flowering plants in containers.

*Plant height* (*soil level to top of foliar plane*).—About 48.6 cm.

*Plant height* (*soil level to top of inflorescences*).—About 74.4 cm.

*Plant width* (*spread*).—About 56.8 cm.

*Stem description*.—Quantity per plant: About eight basal branches per plant. Length: About 34.5 cm. Diameter: About 4.5 mm. Internode length: About 13 cm. Strength: Strong. Aspect: Erect to about 12.5° from vertical. Texture and luster: Sparsely pubescent; pubescence minute; slightly glossy. Color, developing: Close to 144A and 144B. Color, developed: Close to 144A.

LEAF DESCRIPTION:

*Arrangement*.—Alternate; biternately compound; on average, about 37 leaflets per leaf.

*Leaf length* (*excluding petiole*).—About 21.9 cm.

*Leaf width*.—About 19.7 cm.

*Terminal leaflet length*.—About 5 cm.

*Terminal leaflet width*.—About 4.2 cm.

*Lateral leaflet length*.—About 3.1 cm.

*Lateral leaflet width*.—About 2.4 cm.

*Leaf shape, in outline*.—Broadly deltoid to broadly ovate.

*Leaflet shape*.—Broadly ovate.

*Leaflet apex*.—Apiculate.

*Leaflet base*.—Attenuate.

*Leaflet margin*.—Biserrate.

*Leaflet texture and luster, upper surface*.—Sparse pubescence along the midvein and lateral venation; matte.

*Leaflet texture and luster, lower surface*.—Moderate pubescence along the midvein and lateral venation; slightly glossy.

*Leaflet venation pattern*.—Pinnate.

*Leaflet color*.—Developing leaflets, upper and lower surfaces: Close to 144A. Fully expanded leaflets, upper surface: Close to a blend of NN137A and 147A; venation, close to 143C. Fully expanded leaflets, lower surface: Close to 147B; venation, close to 146D.

*Leaf petiole length*.—About 15.4 cm.

*Leaf petiole diameter*.—About 3 mm.

*Leaf and leaflet petiole strength*.—Strong.

*Leaf and leaflet petiole texture and luster, upper and lower surfaces*.—Sparsely pubescent; moderately glossy.

*Leaf and leaflet petiole color, upper surface*.—Close to 144A; at the leaflet nodes, tinged with close to 200C.

*Leaf and leaflet petiole color, lower surface*.—Close to 144A; at the leaflet nodes, tinged with close to 165A.

*Stipules*.—Quantity and arrangement: Two, opposite, at the base of each leaf. Length: About 1.1 cm. Width:

About 4 mm. Shape: Ovate. Apex: Acute. Base: Cuneate. Texture, upper and lower surfaces: Smooth, glabrous. Color, upper and lower surfaces: Close to 166D.

Flower description:

*Flower type and flowering habit*.—Single rotate flowers arranged on mostly upright compound panicles; flowers face upright, outward or downward depending on position on the inflorescence; panicles conical in shape; freely and uniformly flowering habit with about 1,150 flowers developing per inflorescence and about 9,000 flowers developing per plant during the flowering season.

*Fragrance*.—Moderately fragrant; sweet and pleasant.

*Natural flowering season*.—Plants flower continuously from the late spring until the late summer in The Netherlands.

*Postproduction longevity*.—Individual flowers last about ten days on the plant; flowers not persistent.

*Flower buds*.—Height: About 2 mm. Diameter: About 1.5 mm. Shape: Broadly elliptic. Texture and luster: Smooth, glabrous; matte. Color: Close to 144C; towards the apex, strongly tinged with close to 59C.

*Inflorescence height*.—About 29.7 cm.

*Inflorescence diameter*.—About 13.4 cm.

*Flower diameter*.—About 1.7 cm by 1.7 cm.

*Flower depth*.—About 1 cm.

*Petals*.—Quantity per flower: Typically five in a single whorl. Length: About 1 cm. Width: About 1 mm. Shape: Narrowly oblanceolate. Apex: Bluntly acute to obtuse. Base: Narrowly cuneate. Margin: Entire; not undulate. Texture and luster, upper and lower surfaces: Smooth, glabrous; matte. Color: Developing petals, upper and lower surfaces: Close to N78A. Fully expanded petals, upper and lower surfaces: Close to N80B; venation, close to N80B; color becoming closer to N80C with subsequent development.

*Sepals*.—Quantity per flower: Typically five in a single whorl; towards the base forming a campanulate-shaped calyx. Calyx length: About 1.5 mm. Calyx diameter: About 3.5 mm. Length: About 1.5 mm. Width: About 1 mm. Shape: Ovate. Apex: Acute. Base: Cuneate, fused. Margin: Entire. Texture and luster, upper and lower surfaces: Smooth, glabrous; matte. Color: Developing sepals, upper and lower surfaces: Close to 157D; towards the apex and margins, close to 64A. Fully developed sepals, upper and lower surfaces: Close to 145C; towards the apex and margins, close to 61B and 61C.

*Peduncles*.—Length: About 28.7 cm. Diameter: About 3 mm. Angle: Primary peduncles, mostly erect; secondary peduncles, about 45° from primary peduncle axis. Strength: Strong. Texture and luster: Moderately to densely pubescent; moderately glossy. Color: Close to 152D.

*Pedicels*.—Length: About 1 mm. Diameter: About 0.5 mm. Angle: About 40° from peduncle axis. Strength: Moderately strong. Texture and luster: Moderately pubescent; matte. Color: Close to N170D.

*Reproductive organs*.—Stamens: Quantity per flower: Typically ten, occasionally twelve. Filament length: About 4.5 mm. Filament color: Close to N80C. Anther shape: Broadly ovate; basifixed. Anther length: About 0.5 mm. Anther diameter: About 0.35 mm. Anther color: Close to 85B. Pollen amount: Scarce. Pollen color: Close to 156D. Pistils: Quantity per flower: Two. Pistil length: About 2 mm. Stigma diameter: About 0.1 mm. Stigma shape: Club-shaped. Stigma color: Close to 64A. Style length: About 1.75 mm. Style color: Close to 69D. Ovary color: Close to 73C.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures, high light conditions ranging from about −25° C. to about 35° C. and to be suitable for USDA Hardiness Zones 5 through 10.

It is claimed:

1. A new and distinct *Astilbe* plant named 'HVDM18P' as herein illustrated and described.

* * * * *